United States Patent [19]

Kondo

[11] 4,328,184
[45] May 4, 1982

[54] TEST SLIDE STRIP

[75] Inventor: Asaji Kondo, Asaka, Japan

[73] Assignee: Fuji Photo Film Co., Ltd., Kanagawa, Japan

[21] Appl. No.: 208,680

[22] Filed: Nov. 20, 1980

[30] Foreign Application Priority Data

Nov. 30, 1979 [JP] Japan ................ 54-165642

[51] Int. Cl.³ .............. G01N 31/00; G01N 33/52; B65D 69/00
[52] U.S. Cl. .............. 422/58; 206/390; 206/820; 422/56; 435/805
[58] Field of Search .............. 422/56, 58; 206/390, 206/820

[56] References Cited

U.S. PATENT DOCUMENTS

| | | | |
|---|---|---|---|
| 3,162,539 | 12/1964 | Repko | 206/820 X |
| 3,325,050 | 6/1967 | Wanamaker | 206/820 X |
| 3,700,089 | 10/1972 | Halbartschlager | 206/820 X |
| 3,921,802 | 11/1975 | Thompson | 206/820 X |
| 4,125,372 | 11/1978 | Kawai | 23/230 B |
| 4,159,772 | 7/1979 | Beck | 206/820 |
| 4,160,008 | 7/1979 | Fenocketti | 23/230 B X |
| 4,243,144 | 1/1981 | Margulies | 206/820 X |

Primary Examiner—Sidney Marantz
Attorney, Agent, or Firm—Gerald J. Ferguson, Jr.; Joseph J. Baker

[57] ABSTRACT

A plurality of test slides carrying thereon dry reagents for chemical analysis of fluid samples or a dry porous analysis layer are sandwiched and sealed between a continuous base sheet and a continuous cover sheet at equal intervals. A test slide strip having alternately slide holding portions and slide free portions along its length is thus produced. The spaces between the adjacent test slides are longer than the test slides, whereby the test slide strip can be folded in an accordion shape so that the slide holding portions and slide free portions are alternately superposed. The folded test slide strip is nested in a box like casing having a slot in one side wall thereof adjacent the bottom. The test slides are dispensed from the casing through the slot one by one in order by pulling the leading edge of the test slide strip.

5 Claims, 5 Drawing Figures

TEST SLIDE STRIP

BACKGROUND OF THE INVENTION

1. Field of the Invention

This invention relates to a test slide strip containing a plurality of test slides for quantitative analysis of a component of fluid samples and adapted for dispensation of the test slides one by one.

2. Description of the Prior Art

In order to carry out quantitative chemical analysis of fluid samples such as blood a test slide carrying thereon dry reagents is used. The dry reagents are apt to absorb humidity in the atmosphere. Therefore, the test slide should be sealed tight until it is used. Further, it is preferred that the test slides be dispensed one by one in order, especially when the chemical analysis is automatically carried out.

In the U.S. Pat. No. 4,142,863, there is disclosed an article container for dispensing reagent slides. The container includes a generally rectangular casing having a rear wall, a front wall, a pair of side walls, a top wall and a bottom wall. A plurality of reagent slides are stacked on a movable member in the casing. The bottom wall is provided with an opening through which a spring-loaded plunger extends to push the movable member upward so that the uppermost reagent slide in the stack is always pushed against the lower surface of the top wall. The front and rear walls are provided with a slot near the upper edge thereof. A push blade is inserted through the slot in the rear wall to push out the uppermost reagent slide through the slot in the front wall. The container is separated from the spring-loaded plunger when transported or stored. Therefore, the movable member is provided with ratchet pawls which engage with ratchet teeth formed on the inner surface of the casing. The ratchet pawls permit the movable member to be pushed upward by the springloaded plunger, but inhibit downward movement of the movable member when the spring-loaded plunger is removed. In the container, the reagent slides remaining therein are thus prevented from becoming jumbled when the container is removed from the spring-loaded plunger and transported.

The container of the prior art is disadvantageous in that it is costly since its structure is complicated.

Another disadvantage of the container is that the reagent slides are scratched on the ratchet teeth when the slides move upward, with the danger that the reagent on the slide might be contaminated with plastic material scraped off from the periphery of the slide.

Further, since the container does not provide a tight seal for the reagent on the slide, there is the possibility that the reagent may absorb humidity in the atmosphere.

Further, the number of test slides which can be contained in the container is limited since said spring-loaded plunger has to be able to push upward the stack of the test slides either when the container is fully loaded with the test slides or when only one test slide remains in the container.

SUMMARY OF THE INVENTION

In light of the foregoing observation and description, the primary object of the present invention is to provide a test slide strip containing a plurality of test slides in a manner adapted for easy dispensation of the test slides one by one in order.

Another object of the present invention is to provide a test slide strip containing a plurality of test slides in which the reagent or a dry porous analysis layer on the sides is protected from humidity and contaminants in the atomosphere until the slides are actually used to carry out the analysis.

The test slide strip of the present invention comprises a plurality of test slides, a continuous base sheet, and a continuous cover sheet. The test slides are sandwiched and sealed between the base sheet and the cover sheet at equal intervals with blank portions between adjacent test slides so that the strip was alternately slide holding portions and slide free portions along its length. The slide free portion is longer than the test slide, whereby the test slide strip can be folded in an accordion shape so that the slide holding portions and the slide free portions are alternately superposed.

The test slide strip of the present invention is folded as described above and nested in a box like casing which may simply be provided with a slot in a side wall near the bottom thereof and need not be provided with any special provision for locating the test slides or for dispensing them. The folded test slide strip is nested in the casing so that the leading edge of each test slide is disposed adjacent the side wall provided with the slot and the leading edge of the test slide strip projects from the slot. When the leading edge is pulled, the lowermost test slide is drawn through the slot. While the lowermost test slide is being drawn, the remaining test slides are free from being disturbed by virtue of flexibility of the slide free portion between the lowermost test slide and the second lowermost one. When the lowermost test slide is completely drawn out, the remaining test slides are lowered. The test slide strip is severed at the slide free portion between the lowermost test slide and the second lowermost one.

DESCRIPTION OF THE PREFERRED EMBODIMENT

Figure 1:
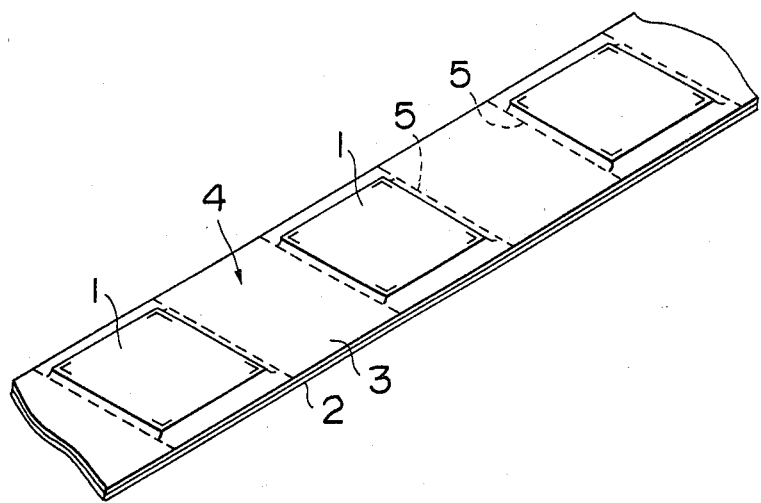
FIG. 1 is fragmentary perspective view of a test slide strip in accordance with an embodiment of the present invention.
Figure 2:
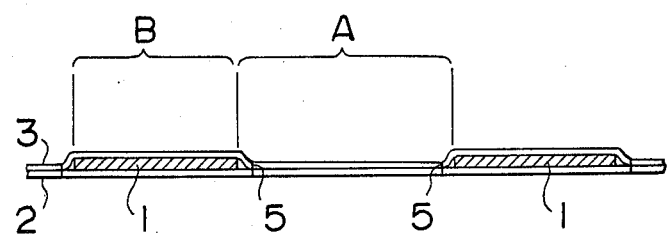
FIG. 2 is a longitudinal section of the test slide strip of FIG. 1.

As shown in FIGS. 1 and 2, a test slide strip in accordance with an embodiment of the present invention includes a continuous base sheet 2 and a continuous cover sheet 3, both sheet 2 and 3 being of transparent polyethylene film. The base sheet 2 and the cover sheet 3 are superposed with each other and a plurality of test slides 1 are sandwiched therebetween at equal intervals with blank portions or slide free portions 4 between adjacent test slides 1. The base sheet 2 and the cover sheet 3 are secured together around each test slide 1 by means of heat seal, for example. The test slide strip thus has alternately slide holding portions and slide free portions 4 along its length.

Transverse perforations 5 are formed in the slide free portion 4 along the leading edge and the rear edge of each test slide 1 so that each test slide 1 can be easily severed.

The length A of said slide free portions 4 is larger than the length B of the test slide 1. With this arrangement the test slide strip of this invention can be folded in an accordion shape so that the slide holding portions and the slide free portions 4 are alternately superposed.

Figure 3:
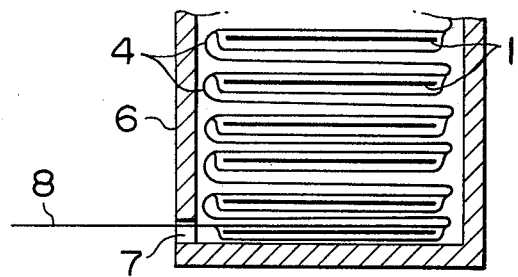
FIG. 3 is a view showing the test slide strip of FIG. 1 folded and nested in a casing.

The folded test slide strip is nested in a box like casing 6 provided with a slot 7 in one side wall adjacent its bottom so that the leading edge of each test slide 1 is disposed adjacent said one side wall with the leading edge portion 8 of the test slide strip, which is one of the slide free portions 4, projecting outside through the slot 7 as shown in FIG. 3.

Figure 4:
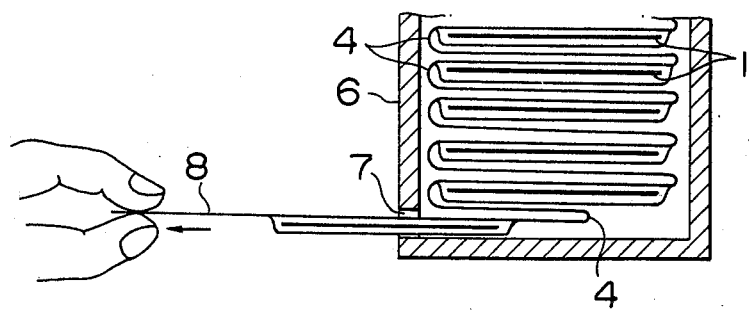
FIG. 4 shows the lowermost test slide partly drawn from the casing.

When the leading edge portion 8 of the test slide strip is pulled, the lowermost test slide 1 is drawn through the slot 7 as shown in FIG. 4. While the lowermost test slide is drawn, the remaining test slides keep their position by virtue of the flexibility of the slide free portion 4 between the lowermost test slide and the second lowermost one.

Figure 5:
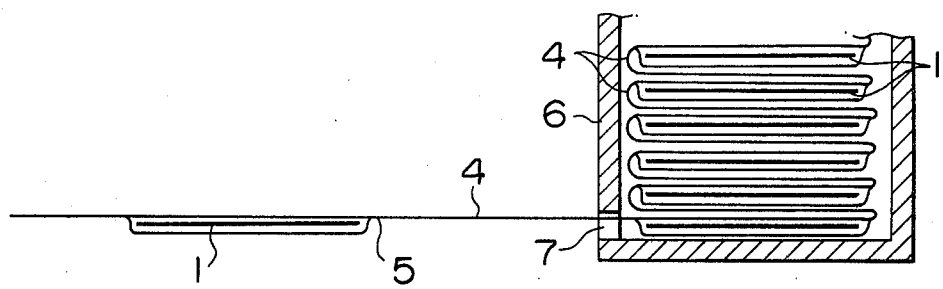
FIG. 5 shows the lowermost test slide completely drawn out from the casing.

After the lowermost test slide 1 is completely drawn outside the casing 6, the lowermost test slide 1 is severed along the perforation 5 adjacent the rear edge thereof as shown in FIG. 5. After the lowermost test slide 1 is severed along the perforation 5, the slide free portion 4 between the lowermost test slide 1 and the second lowermost one remains projecting outside the casing 6, whereby the second lowermost test slide 1 can be drawn by pulling the slide free portion 4.

It is not essential for the test slide strip of the present invention to be provided with the perforations 5. However, by providing the test slide strip with the perforations 5 each test slide 1 can easily be severed. Further, the perforations 5 may be provided only on one side of each test slide 1. However, in this case, the folded test slide strip has to be positioned in the casing 6 so that the perforations 5 are disposed remote from the side wall of the casing 6 provided with the slot 7, since the test slide 1 is always severed on the rear edge side.

Although, the base sheet 2 and the cover sheet 3 are of transparent polyethylene in the above embodiment, the sheets may be of any suitable flexible material such as paper and polyethylene coated aluminum foil. However, the sheets 2 and 3 are preferred to be of transparent polyethlene, sheets are easily secured together by heat are easily secured together by heat processing and also the test slides 1 sandwiched therebetween can be viewed from the outside.

As can be seen from the above description, the test slide strip of the present invention can be readily automatically produced. Further, the test slide strip of the present invention enables test slides to be dispensed one by one in order from a simple box like casing having a slot, and therefore, a complicated dispensing device is no more required. Further, since the test slides are sandwiched and sealed between the base sheet and the cover sheet, they are protected from humidity or any contaminant in the atmosphere until they are actually used.

I claim:

1. A test slide strip comprising a plurality of quantitative analysis slides for analysis of a component of fluid samples, a continuous base sheet and a continuous cover sheet, said test slides being sandwiched and sealed between the base sheet and the cover sheet at equal intervals with blank portions between adjacent test slides so that the test slide strip has alternately slide holding portions and slide free portions along its length, said slide free portions being longer than the test slide, whereby the slide strip can be folded in an accordion shape so that the slide holding portions and the slide free portions are alternately superposed.

2. A test slide strip as defined in claim 1 in which said quantitative analysis slides are reagent slides for chemical analysis.

3. A test slide strip as defined in claims 1 or 2 in which said base sheet and said cover sheet are of transparent polyethylene film.

4. A test slide strip as defined in claims 1, 2 or 3 in which transverse perforations are provided in said slide free portion along the rear edge of each test slide.

5. A test slide as defined in claim 4 in which additional transverse perforations are provided in said slide free portion along the leading edge of each test slide.

* * * * *